(12) United States Patent
Akagane

(10) Patent No.: US 11,510,727 B2
(45) Date of Patent: Nov. 29, 2022

(54) TREATMENT INSTRUMENT AND MANUFACTURING METHOD OF TREATMENT INSTRUMENT

(71) Applicant: OLYMPUS CORPORATION, Hachioji (JP)

(72) Inventor: Tsunetaka Akagane, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 633 days.

(21) Appl. No.: 16/538,921

(22) Filed: Aug. 13, 2019

(65) Prior Publication Data

US 2019/0357970 A1    Nov. 28, 2019

Related U.S. Application Data

(63) Continuation of application No. PCT/JP2017/005858, filed on Feb. 17, 2017.

(51) Int. Cl.
*A61B 18/14* (2006.01)
*B32B 7/12* (2006.01)
(Continued)

(52) U.S. Cl.
CPC ............ *A61B 18/1445* (2013.01); *B32B 7/12* (2013.01); *H05B 3/03* (2013.01); *H05B 3/06* (2013.01);
(Continued)

(58) Field of Classification Search
CPC ........... A61B 2018/00095; A61B 2018/00077; A61B 2018/00083; A61B 2018/00589;
(Continued)

(56) References Cited

U.S. PATENT DOCUMENTS

| 5,352,222 A | * | 10/1994 | Rydell | ............... A61B 18/1445 606/174 |
| 2012/0330310 A1 | * | 12/2012 | Takashi | ............... A61B 18/148 606/45 |

(Continued)

FOREIGN PATENT DOCUMENTS

| JP | 2015-097595 | * | 5/2015 |
| JP | 2015-097595 A | | 5/2015 |

(Continued)

OTHER PUBLICATIONS

Apr. 4, 2017 International Search Report issued in International Application No. PCT/JP2017/005858.

(Continued)

*Primary Examiner* — Shawntina T Fuqua
(74) *Attorney, Agent, or Firm* — Oliff PLC

(57) ABSTRACT

A treatment instrument including a heat transmitter that includes a treating surface and an installation surface, a substrate attached to the installation surface, and a heat generator formed on a surface of the substrate. The substrate surface and heat generator together form an uneven surface. First and second adhesion layers formed of a material having thermal conductivity and electrical insulation are provided between the installation surface and the substrate. The first adhesion layer is in close contact with the installation surface, and the second adhesion layer is in close contact with the heat generator and the substrate surface. The second adhesion layer is inserted into a recess in the uneven surface formed by the heat generator on substrate surface so as to increase the contact area between the second adhesion layer and the uneven surface.

18 Claims, 4 Drawing Sheets

(51) Int. Cl.
   *H05B 3/03* (2006.01)
   *H05B 3/06* (2006.01)
   *H05B 3/36* (2006.01)
   *A61B 17/00* (2006.01)
   *A61B 18/00* (2006.01)

(52) U.S. Cl.
   CPC ...... *H05B 3/36* (2013.01); *A61B 2017/00526* (2013.01); *A61B 2018/00077* (2013.01); *A61B 2018/00083* (2013.01); *A61B 2018/00095* (2013.01); *H05B 2203/017* (2013.01)

(58) Field of Classification Search
   CPC .. A61B 2018/1455; A61B 2018/00595; A61B 2018/00994; A61B 2018/00577; A61B 2018/1266; A61B 2018/00607; A61B 2018/00196; A61B 18/085; A61B 18/1445; A61B 2017/00526; H05B 2203/017; H05B 3/26; H05B 3/36; H05B 3/03; H05B 3/06; B32B 3/30; B32B 2307/302; B32B 2307/206; B32B 2457/00; B32B 27/08; B32B 27/20; B32B 27/281; B32B 2264/107; B32B 2535/00; B32B 7/12

See application file for complete search history.

(56) References Cited

U.S. PATENT DOCUMENTS

| | | |
|---|---|---|
| 2016/0324566 A1 | 11/2016 | Kudo |
| 2021/0196353 A1* | 7/2021 | Gee ........................ A61B 90/03 |
| 2021/0196367 A1* | 7/2021 | Salguero ............ A61B 18/1206 |

FOREIGN PATENT DOCUMENTS

| | | | |
|---|---|---|---|
| WO | 2016/167196 | * | 10/2016 |
| WO | 2016/167196 A1 | | 10/2016 |

OTHER PUBLICATIONS

Aug. 20, 2019 International Preliminary Report on Patentability issued in International Application No. PCT/JP2017/005858.

\* cited by examiner

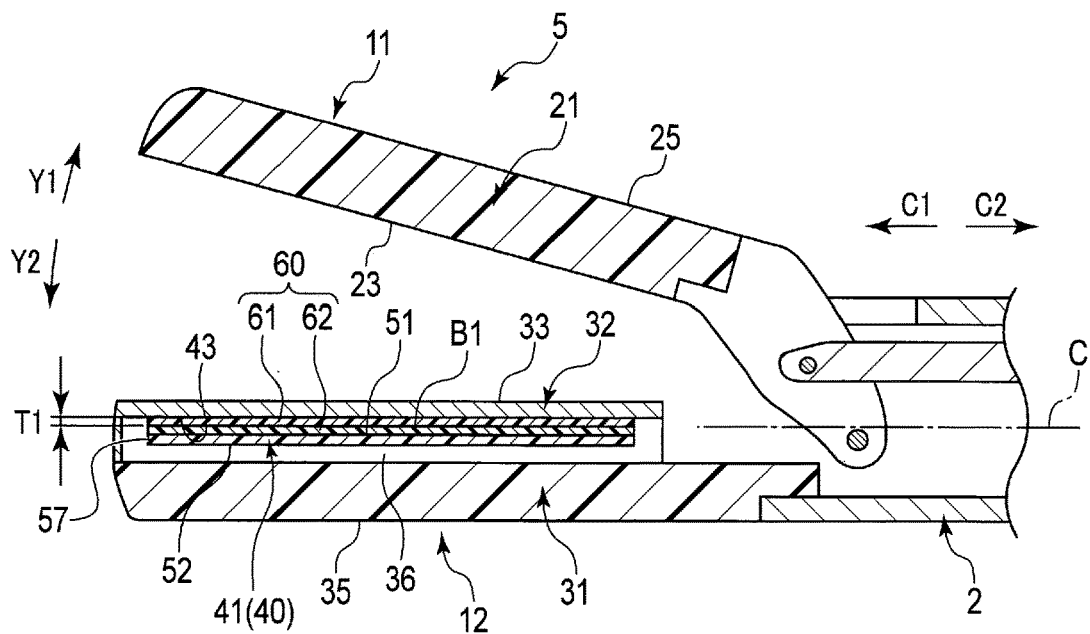
F I G. 2
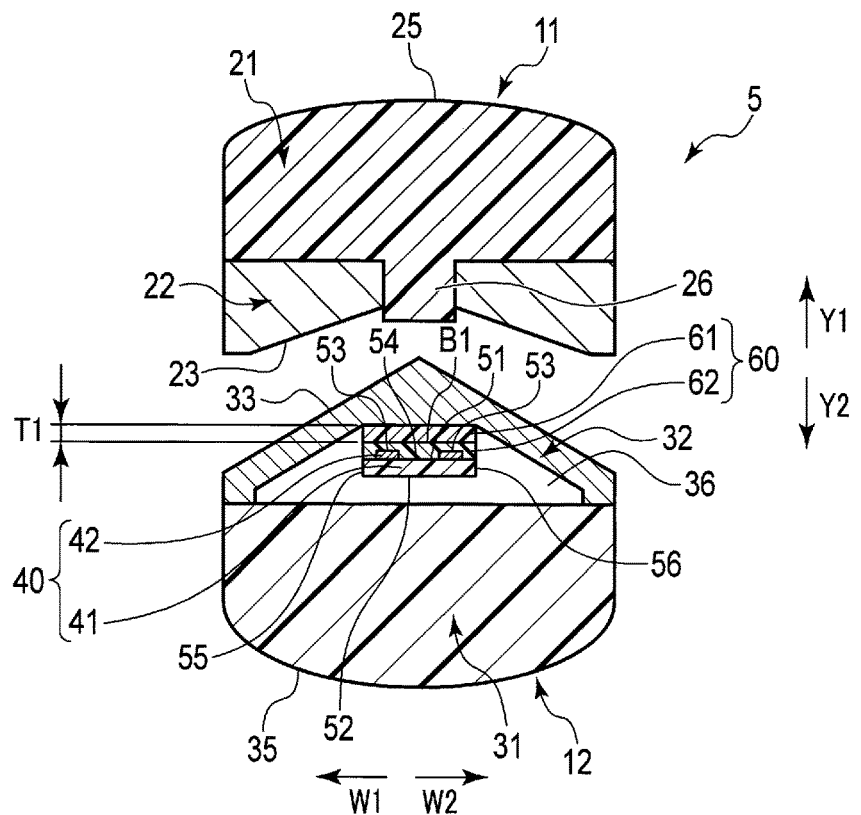
F I G. 3

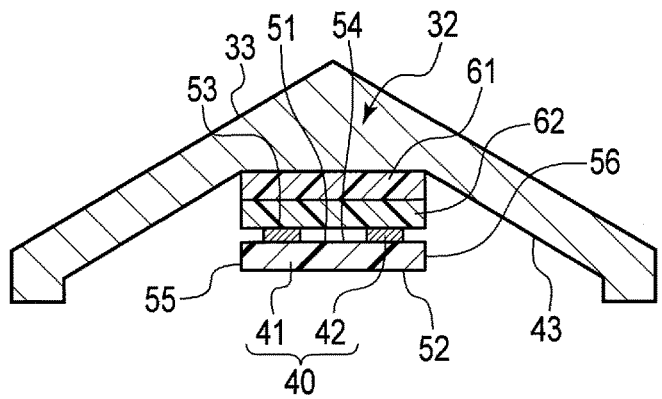
F I G. 4
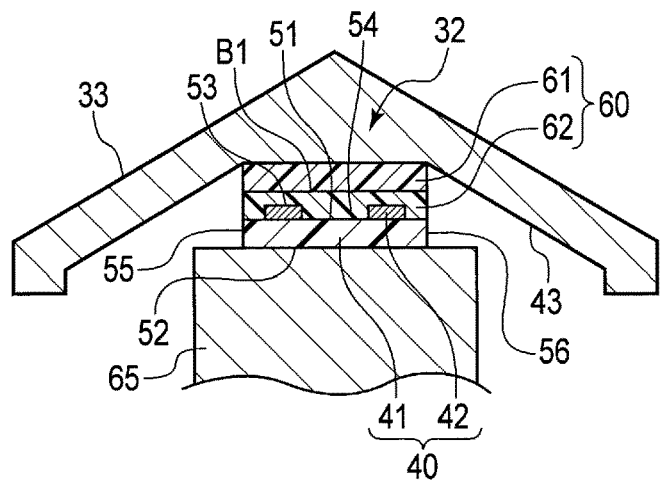
F I G. 5
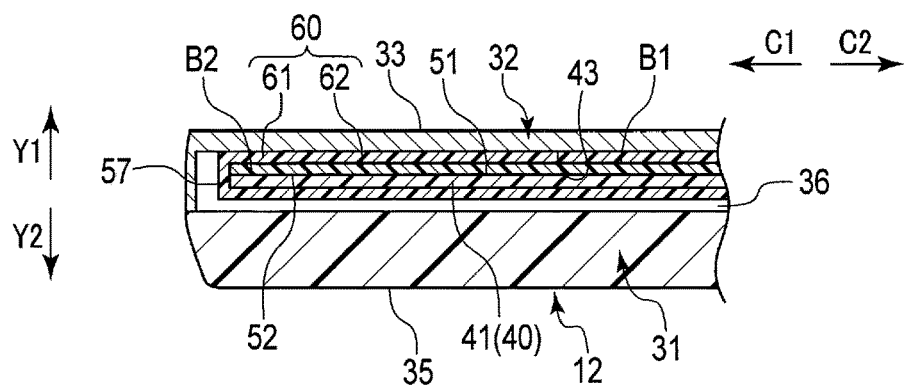
F I G. 6

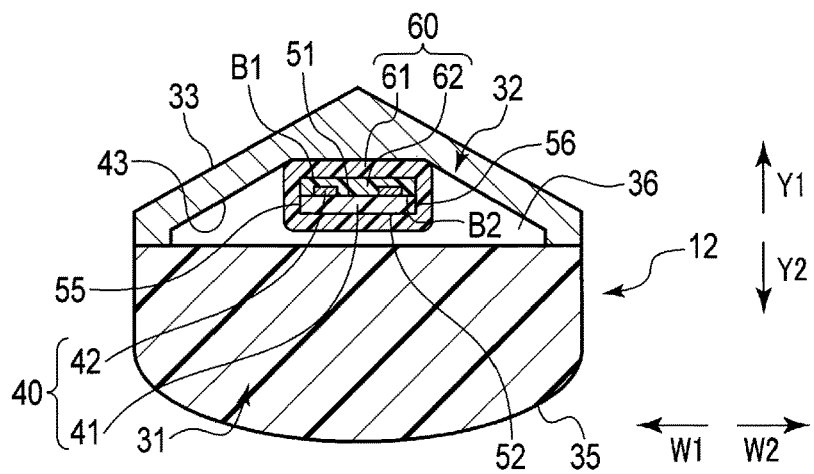
F I G. 7
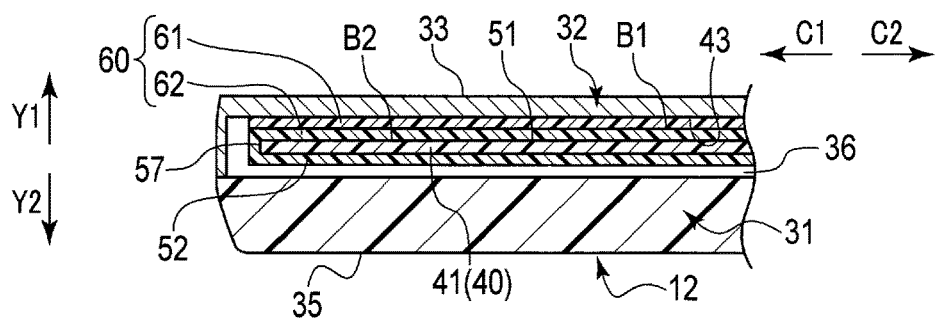
F I G. 8
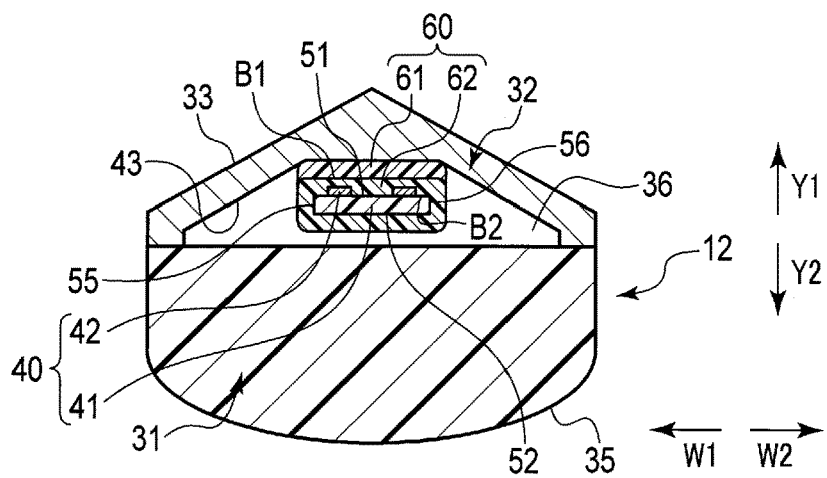
F I G. 9

TREATMENT INSTRUMENT AND MANUFACTURING METHOD OF TREATMENT INSTRUMENT

CROSS-REFERENCE TO RELATED APPLICATIONS

This is a Continuation Application of PCT Application No. PCT/JP2017/005858, filed Feb. 17, 2017, the entire contents of which are incorporated herein by reference.

The present disclosure relates to a treatment instrument that performs a treatment using heat generated by a heat generator and a high-frequency current, and relates to a manufacturing method of this treatment instrument.

BACKGROUND

There are treatment instruments in which a pair of grasping pieces can be opened and closed. In such treatment instruments, electric energy can be transferred to treatment surfaces of the grasping pieces to treat a treatment target grasped between the pair of grasping pieces. For example, a high-frequency current may flow between the grasping pieces through the treatment target held by the grasping pieces. When the electric energy is properly transmitted to the treatment surfaces, the treatment target may be appropriately treated.

BRIEF SUMMARY

The present disclosure is directed to a treatment instrument including: a heat transmitter including a treating surface and an installation surface, a substrate attached to the installation surface of the heat transmitter, and a heat generator formed on a surface of the substrate. The substrate surface and the heat generator together form an uneven surface. First and second adhesion layers formed of a material having thermal conductivity and electrical insulation are provided between the installation surface of the heat transmitter and the substrate. The first adhesion layer is in close contact with the installation surface of the heat transmitter, and the second adhesion layer is in contact with the heat generator and the substrate surface such that the second adhesion layer is inserted into a recess in the uneven surface formed by the heat generator on the substrate surface.

The present disclosure also relates to a method of manufacturing a treatment instrument. The method may include forming a heat generator on a substrate surface such that the substrate surface and the heat generator together form an uneven surface. The substrate may be disposed on an installation surface of a heat transmitter such that the substrate surface faces the heat transmitter, a first adhesion layer formed of a material having thermal conductivity and electrical insulation is diposed between the installation surface of the heat transmitter and the substrate, and a second adhesion layer formed of a material having thermal conductivity and electrical insulation is disposed between the substrate and the first adhesion layer. The first adhesion layer and the second adhesion layer may be heated to soften the first adhesion layer and the second adhesion layer, and thereby form a state in which the second adhesion layer is softer than the first adhesion layer. The substrate may be pressed toward the heat transmitter in a state in which the first adhesion layer and the second adhesion layer have been softened to bring the first adhesion layer into contact with the installation surface of the heat transmitter. The second adhesion layer is inserted into a recess formed in the uneven surface formed by the substrate surface and the heat transmitter so that the second adhesion layer is brought into contact with the heat generator and the substrate transmitter. Heating of the first adhesion layer and the second adhesion layer may be continued in a state in which the first adhesion layer is in contact with the installation surface and the second adhesion layer is in contact with the heat generator and the substrate surface to cure the first adhesion layer and the second adhesion layer, and thereby attach the substrate to the installation surface of the heat transmitter through the first adhesion layer and the second adhesion layer.

Advantages will be set forth in the description which follows, and in part will be apparent from the description, or may be learned by practice. The advantages may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate exemplary embodiments, and together with the general description given above and the detailed description of the embodiments given below, serve to explain the inventive principles.

FIG. 2 is a cross-sectional view schematically showing an end effector according to an exemplary embodiment in a cross section substantially perpendicular to the width direction, FIG. 3 is a cross-sectional view schematically showing the end effector according to an exemplary embodiment in a cross section substantially perpendicular to the direction along the longitudinal axis, FIG. 4 is a cross-sectional view schematically showing the state in which a substrate, a first adhesion layer, and a second adhesion layer are arranged on the installation surface of a heat transmitting member in manufacture of the treatment instrument according to an exemplary embodiment, FIG. 5 is a cross-sectional view schematically showing the state in which the first adhesion layer and the second adhesion layer are softened by heating from the state of FIG. 4, and the substrate and the softened adhesion layers are pressed toward the installation surface of a heat transmitting member, FIG. 6 is a cross-sectional view schematically showing, in a cross section substantially perpendicular to the width direction, one grasping piece according to an exemplary embodiment, FIG. 7 is a cross-sectional view schematically showing, in a cross section substantially perpendicular to the direction along the longitudinal axis, one grasping piece according to an exemplary embodiment, FIG. 8 is a cross-sectional view schematically showing, in a cross section substantially perpendicular to the width direction, one grasping piece according to an exemplary embodiment, and FIG. 9 is a cross-sectional view schematically showing, in a cross section substantially perpendicular to the direction along the longitudinal axis, one grasping piece according to an exemplary embodiment.

DETAILED DESCRIPTION

Figure 1:
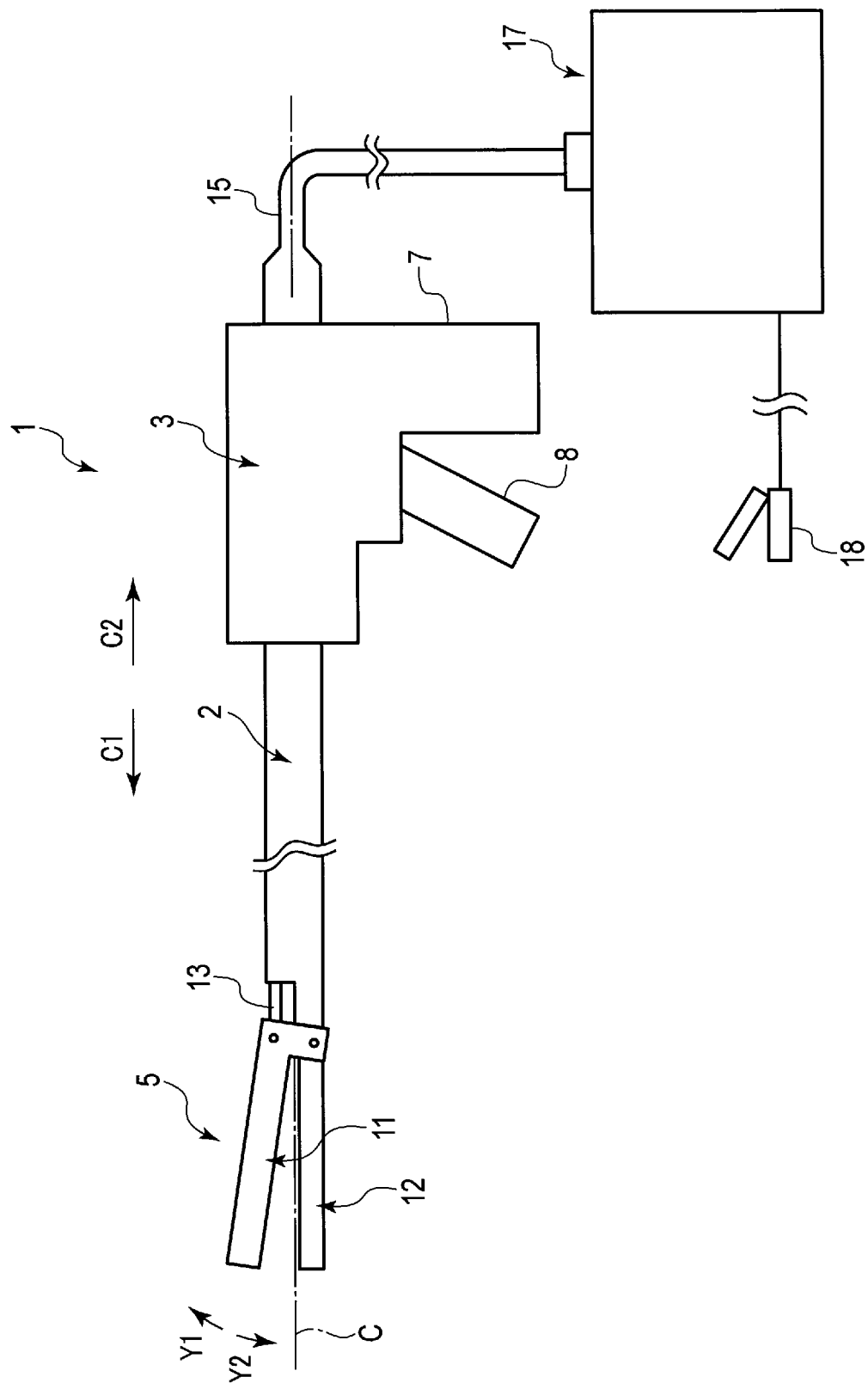
FIG. 1 is a schematic view showing a system in which a treatment instrument according to an exemplary embodiment is used.

An exemplary embodiment will be described with reference to FIGS. 1 to 5. FIG. 1 is a diagram showing a system in which a treatment instrument 1 of the present embodiment is used. As shown in FIG. 1, the treatment instrument 1 includes a shaft 2, a housing 3 and an end effector (grasping unit) 5. The shaft 2 has a longitudinal axis C as a central axis, and extends along the longitudinal axis C. Here, one side in the direction along the longitudinal axis C is referred to as the distal side (arrow C1 side), and the side opposite to the distal side is referred to as the proximal side (arrow C2 side). The housing 3 is connected to the proximal side of the shaft 2. Further, the end effector 5 is provided at the distal portion of the shaft 2.

The housing 3 includes a grip 7 extending along a direction intersecting with the longitudinal axis C, and a handle 8 is pivotably attached to the housing 3. The handle 8 pivots relative to the housing 3, so that the handle 8 opens or closes with respect to the grip 7. In the embodiment of FIG. 1, the handle 8 is located on the grip 7 side with respect to the longitudinal axis C, and is located on the distal side with respect to the grip 7. The handle 8 moves substantially parallel to the longitudinal axis C in the opening motion and the closing motion of the handle 8. However, the handle 8 may be located on the proximal side relative to the grip 7. Also, in another embodiment, the handle 8 may be located on the side opposite to the grip 7 side with respect to the longitudinal axis C, and in the opening motion and the closing motion of the handle 8, the handle 8 is moved in a direction intersecting with (substantially perpendicular to) the longitudinal axis C. Also, in an embodiment, an operation member (not shown) such as a rotation knob may be attached to the housing 3, and by rotating the rotation knob around the longitudinal axis C, the shaft 2 and the end effector 5 may together rotate around the longitudinal axis C relative to the housing 3.

The end effector 5 includes a pair of grasping pieces (jaw) 11 and 12. Here, one of the grasping pieces 11 and 12 may be integrally formed with the shaft 2 or fixed to the shaft 2, and the other of the grasping pieces 11 and 12 may be pivotably attached to the shaft 2. For example, in the embodiment of FIG. 1, the grasping piece 11 is pivotably attached to the shaft 2 and the grasping piece 12 is fixed to the shaft 2. Also, in another embodiment, both the grasping pieces 11 and 12 may be pivotably attached to the shaft 2. Inside the shaft 2, a movable member 13 extends from the proximal side toward the distal side, and the distal portion of the movable member 13 is connected to the end effector 5. The proximal portion of the movable member 13 is connected to the handle 8 inside the housing 3. The movable member 13 moves along the longitudinal axis C by opening or closing the handle 8 relative to the grip 7. Thereby, at least one of the grasping pieces 11 and 12 pivots relative to the shaft 2, and the space between the grasping pieces 11 and 12 opens and closes. Since it is possible to open and close the space between the grasping pieces 11 and 12, a treatment target such as a living tissue can be gripped between the grasping pieces 11 and 12. The respective movement directions (directions indicated by the arrows Y1 and Y2) in the opening motion and the closing motion of an end effector 5 intersect (substantially perpendicular) with the direction along the longitudinal axis C.

One end of a cable 15 is connected to the housing 3 of the treatment instrument 1. The other end of the cable 15 is connected to an energy source device 17 separate from the treatment instrument 1. Moreover, an operation member 18 is provided in the system in which the treatment instrument 1 is used. In the embodiment of FIG. 1, the operation member 18 is a foot switch separate from the treatment instrument 1 and is electrically connected to the energy source device 17. The energy source device 17 supplies electric energy to the treatment instrument 1 based on the operation of the operation member 18. By supplying electric energy from the energy source device 17 to the treatment instrument 1, treatment energy is applied to the treatment target held between the grasping pieces 11 and 12 as described later. In an embodiment, as the operation member 18, instead of or in addition to the foot switch, operation buttons or the like attached to the housing 3 may be provided.

FIGS. 2 and 3 are diagrams showing the configuration of the end effector 5. Here, the width direction of the end effector 5 (direction indicated by arrow W1 and arrow W2) which intersects with (substantially perpendicular to) the direction along the longitudinal axis C and intersects with (substantially perpendicular to) the movement direction in each of the opening operation and the closing motions of the end effector 5 is defined. FIG. 2 shows the end effector 5 in a section substantially perpendicular to the width direction, and FIG. 3 shows the end effector 5 in a section substantially perpendicular to the direction along the longitudinal axis C.

As shown in FIGS. 2 and 3, the grasping piece 11 includes a support body 21 attached to the shaft 2 and an electrically conductive member 22 fixed to the support body 21. The electrically conductive member 22 is formed of a metal or the like having electrical conductivity, and is attached to the support body 21 from the grasping piece 12 side. Each of the support body 21 and the electrically conductive member 22 extends in the direction along the longitudinal axis C from the proximal portion to the distal portion of the grasping piece 11. In addition, the grasping piece 11 includes a facing surface 23 facing the grasping piece 12, and a back surface 25 facing the opposite side to the facing surface 23. In the present embodiment, the back surface 25 is formed by the support body 21, and the facing surface 23 is formed by the support body 21 and the electrically conductive member 22.

The support body 21 includes a protrusion 26 protruding toward the grasping piece 12 side, and the protrusion 26 forms part of the facing surface 23. The electrically conductive member 22 is provided on both sides of the protrusion 26 in the width direction of the end effector 5 (the width direction of the grasping piece 11). The electrically conductive member 22 is connected to one end of an electric supply path (not shown) formed of electrical wiring or the like. The electric supply path extends through the interior of the shaft 2, the interior of the housing 3 and the interior of the cable 15, the other end is connected to the energy source device 17. In the support body 21, at least a portion in contact with the electrically conductive member 22 and a portion forming the facing surface 23 are formed of an electrically insulating material. Thus, the support body 21 is electrically isolated from the electrically conductive member 22. In the embodiment of FIGS. 2 and 3, the entire support body 21, including the protrusion 26, is formed of an electrically insulating material. In addition, the support body 21 is preferably formed of a material having low thermal conductivity.

The grasping piece 12 includes a support body 31 attached to the shaft 2, and a heat transmitting member (blade) 32 fixed to the support body 31. The heat transmitting member 32 is formed of a material having high thermal conductivity such as copper alloy or aluminum alloy, and has electrical conductivity. Further, the heat transmitting member 32 is attached to the support body 31 from the grasping piece 11 side. Each of the support body 31 and the heat transmitting member 32 extends in the direction along the longitudinal axis C from the proximal portion to the distal portion of the grasping piece 12. Further, the grasping piece 12 has a treating surface (facing surface) 33 facing the facing surface 23 of the grasping piece 11, and a back surface 35 being opposite to the treating surface 33. In the present embodiment, the back surface 35 is formed by the support body 31, and the treating surface 33 is formed by the heat transmitting member 32.

Further, a cavity 36 surrounded by the heat transmitting member 32 and the support body 31 is formed in the inside of the grasping piece 12. The cavity 36 is formed in the range from the proximal portion to the distal portion of the grasping piece 12 in the direction along the longitudinal axis C. The heat transmitting member 32 is adjacent to the cavity 36 from the distal side, the treating surface 33 side, and both sides in the width direction of the end effector 5. Also, the support 31 is adjacent to the cavity 36 from the back surface 35 side. One end of an electric supply path (not shown) formed of electrical wiring or the like is connected to the heat transmitting member 32. The electric supply path extends through the interior of the shaft 2, the interior of the housing 3 and the interior of the cable 15, the other end is connected to the energy source device 17. In the support body 31, at least a portion in contact with the heat transmitting member 32 and a portion adjacent to the cavity 36 are formed of an electrically insulating material. Thus, the support body 31 is electrically isolated from the heat transmitting member 32. In the embodiment of FIGS. 2 and 3, the entire support body 31 is formed of an electrically insulating material. Further, the support 31 body is preferably formed of a material having low thermal conductivity.

The energy source device 17 outputs high-frequency electric power as electric energy based on the operation of the operation member 18. The output high-frequency electric power is supplied to the electrically conductive member 22 of the grasping piece 11 through the aforementioned electric supply path, and is supplied to the heat transmitting member 32 of the grasping piece 12 through the aforementioned electric supply path. Thus, the electrically conductive member 22 and the heat transmitting member 32 function as electrodes having different electrical potentials with respect to each other. The electrically conductive member 22 and the heat transmitting member 32 function as electrodes while holding the treatment target between the grasping pieces 11 and 12, so that a high-frequency current flows between the electrically conductive member 22 and the heat transmitting member 32 through the treatment target, and a high-frequency current is applied to the treatment target as treatment energy.

Further, in a state in which the space between the grasping pieces 11 and 12 is closed, the heat transmitting member 32 can contact the protrusion 26 of the support body 21 at the facing surface 23 of the grasping piece 11. In a state in which the heat transmitting member 32 contacts the protrusion 26 of the support body 21, a gap is formed between the heat transmitting member 32 and the electrically conductive member 22, and the heat transmitting member 32 does not contact the electrically conductive member 22. For this reason, in a state in which the electrically conductive member 22 and the heat transmitting member 32 function as electrodes, a short circuit in the electrical circuit of the electric energy output from the energy source device 17 to the heat transmitting member 32 and the electrically conductive member 22 is effectively suppressed.

In the embodiment shown in FIGS. 2 and 3, the facing surface 23 of the grasping piece 11 is formed in a concave shape in which the central portion in the width direction is concave toward the back surface 25 side, and the treating surface 33 of the grasping piece 12 is formed in a convex shape in which a central portion in the width direction protrudes toward the grasping piece 11. However, in an embodiment, the facing surface 23 of the grasping piece 11 extends substantially parallel to the width direction of the end effector 5. Also, in another embodiment, the facing surface 23 of the grasping piece 11 may be formed in a convex shape in which the central portion in the width direction protrudes toward the grasping piece 12, and the treating surface 33 of the grasping piece 12 is formed in a concave shape in which the central portion in the width direction is concave toward the back surface 35 side.

A heat generating module 40 is disposed in the cavity 36 of the grasping piece 12. The heat generating module 40 includes a substrate 41 and a heat generator 42 provided on the substrate 41. Each of the substrate 41 and the heat generator 42 extends in a range from the proximal portion to the distal portion of the grasping piece 12 in the direction along the longitudinal axis C. The substrate 41 is a flexible substrate formed of, for example, a resin such as polyimide, and has electrical insulation. The heat generator 42 is a heating wire attached to the substrate 41, a heating pattern printed on the substrate 41 or the like, and is made of nichrome alloy, stainless steel alloy or the like.

The heat transmitting member (blade) 32 has an installation surface 43 being opposite to the treating surface 33, that is, facing the back surface 35 side. The installation surface 43 is adjacent to the cavity 36 from the treating surface 33 side. The heat generating module 40 including the substrate 41 and the heat generator 42 is attached to the installation surface 43 of the heat transmitting member 32 from the back surface 35 side. Here, the substrate 41 includes a substrate front surface 51 on which the heat generator 42 is formed, and a substrate back surface 52 being opposite to the substrate front surface 51. The substrate front surface 51 faces one side in the thickness direction of the substrate 41. By forming the heat generator 42 on the substrate front surface 51, on the substrate front surface 51, a protrusion 53 protruding toward the outside of the substrate 41 is formed at a portion where the heat generator 42 extends. In the substrate front surface 51, a recess 54 that is recessed toward the inside of the substrate 41 is formed in a portion where the heat generator 42 does not extend. For this reason, the substrate front surface 51 is formed to be uneven by the heat generator 42.

The substrate 41 has a first substrate side surface 55 disposed at one side in the width direction of the substrate 41, and a second substrate side surface 56 disposed opposite to the first substrate side surface 55. The heat generating module 40 is attached to the installation surface 43 in a state in which the thickness direction of the substrate 41 is substantially parallel to the movement direction in each of the opening motion and the closing motion of the end effector 5, and the width direction of the substrate 41 is substantially parallel to the width direction of the end effector 5. The heat generating module 40 is attached to the installation surface 43 in a state in which the substrate front surface 51 faces the heat transmitting member 32 side, that is, in a state in which the substrate front surface 51 faces the treating surface 33 side. Further, the substrate 41 has a substrate distal surface 57 which forms the distal end of the substrate 41. The substrate distal surface 57 is located at the distal portion of the cavity 36 and faces the distal side. The cavity 36 forms a gap between the substrate back surface 52 of the substrate 41 and the support body 31. The cavity 36 forms a gap between the heat transmitting member 32 and each of the substrate side surfaces 55 and 56 and the substrate distal surface 57.

The heat generator 42 has two connection terminals (not shown), and these connection terminals are disposed at the proximal portion of the grasping piece 12. One of the connection terminals is connected to one end of an electric supply path (not shown) formed of electrical wiring or the like, and the other of the connection terminals is connected to one end of another electric supply path (not shown) formed of electrical wiring or the like. Each of the electric supply paths extends through the interior of the shaft 2, the interior of the housing 3 and the interior of the cable 15, and the other end is connected to the energy source device 17. The heat generator 42 has a return position (not shown), and the return position is disposed at the distal portion of the grasping piece 12. At the substrate front surface 51, the heat generator 42 extends toward the distal side from one of the connection terminals to the return position, and the heat generator 42 extends toward the proximal side from the return position to the other connection terminal.

Based on the operation of the operation member 18, the energy source device 17 outputs DC power or AC power as electric energy different from the high-frequency electric power supplied to the electrically conductive member 22 and the heat transmitting member 32. The output DC power or AC power is supplied to the heat generator 42 through the above-described electric supply path. As a result, the electric energy supplied to the heat generator 42 is converted into heat energy due to the resistance of the heat generator 42, and heat is generated in the heat generator 42.

In the cavity 36 of the grasping piece 12, a first adhesion layer 61 is provided between the installation surface 43 of the heat transmitting member 32 and the substrate front surface 51 of the substrate 41, and a second adhesion layer 62 is provided between the substrate front surface 51 of the substrate 41 and the first adhesion layer 61. Each of the adhesion layers 61 and 62 extends in the range from the proximal portion to the distal portion of the grasping piece 12 in the direction along the longitudinal axis C. The heat generating module 40 including the substrate 41 and the heat generator 42 is attached to the installation surface 43 of the heat transmitting member 32 through the adhesion layers 61 and 62. Each of the adhesion layers 61 and 62 is, for example, an adhesion sheet, and is formed of a material having high thermal conductivity and electrical insulation.

The first adhesion layer 61 is in close contact with the installation surface 43 of the heat transmitting member 32 from the back surface 35 side. The first adhesion layer 61 is in close contact with the second adhesion layer 62 from the treating surface 33 side. The first adhesion layer 61 adheres to the installation surface 43 and the second adhesion layer 62 over substantially the entire length from the proximal portion to the distal portion in the direction along the longitudinal axis C. The second adhesion layer 62 is in close contact with the substrate front surface 51 of the substrate 41 and the heat generator 42 from the treating surface 33 side, that is, from the heat transmitting member 32 side. The second adhesion layer 62 is in close contact with the substrate front surface 51 over substantially the entire length from the proximal portion to the distal portion in the direction along the longitudinal axis C, the entire substrate front surface 51 including the heat generator 42 is not exposed to the cavity 36 because the adhesion of the second adhesion layer 62. Also, the second adhesion layer 62 is inserted into the recess 54 at the uneven substrate front surface 51 as described above. Since the second adhesion layer 62 is inserted into the recess 54, the contact area between the substrate front surface 51 and the second adhesion layer 62 is large.

Although the substrate front surface 51 including the heat generator 42 is in close contact with the second adhesion layer 62, the substrate front surface 51 does not contact the first adhesion layer 61 and the heat transmitting member 32. Therefore, the heat generator 42 is electrically insulated from the heat transmitting member 32 by the adhesion layers 61 and 62. Therefore, electrical conduction between the electrical circuit of the electric energy supplied to the electrically conductive member 22 and the heat transmitting member 32 (high-frequency electric power) and the electrical circuit of the electric energy supplied to heat generator 42 (DC power or AC power) is effectively suppressed. That is, the adhesion layers 61 and 62 form an electrically insulating portion 60 between the substrate front surface 51 (heat generator 42) and the heat transmitting member 32.

In addition, a boundary B1 between the adhesion layers 61 and 62 is located closer to the installation surface 43 with respect to the top of any protrusion 53 of the substrate front surface 51. For this reason, the first adhesion layer 61 is not inserted into the recess 54 of the uneven substrate front surface 51. Therefore, the top of any protrusion 53 of the substrate front surface 51 is disposed away from the installation surface 43 by the thickness T1 or more of the first adhesion layer 61 by the first adhesion layer 61. That is, the electrically insulating portion 60 between the substrate front surface 51 and the installation surface 43 has a dimension in the thickness direction which is equal to or greater than the thickness T1 of the first adhesion layer 61 at any position. Further, the heat generated by the heat generator is transmitted to the treating surface 33 through the second adhesion layer 62, the first adhesion layer 61 and the heat transmitting member 32 in this order. The heat transmitted as treatment energy is applied to the treatment target held between the grasping pieces 11 and 12 through the treating surface 33.

Each of the adhesion layers 61 and 62 is formed of, for example, a mixture of a thermosetting resin such as an epoxy resin and a ceramic powder. Since each of the adhesion layers 61 and 62 contains a thermosetting resin, the material forming each of the adhesion layers 61 and 62 soften by heating, and by continuing heating after softening once, it is cured by the chemical change in the thermosetting resin. In the treatment instrument 1 as a product, each of the adhesion layers 61 and 62 is provided in a cured state by a chemical change in the thermosetting resin. The material forming each of the adhesion layers 61 and 62 does not soften or melt even if it is heated again after cooling, once it is cured by the chemical change in the thermosetting resin. Therefore, with treatment instrument 1, even if the temperature of the adhesion layers 61 and 62 rises due to the heat generated by the heat generator 42, each of the adhesion layers 61 and 62 does not soften or melt.

In addition, in the adhesion layers 61 and 62, at least one of the ingredient of the thermosetting resin, the content of the ceramic, the size of the ceramic powder, and the like are different from each other. For this reason, in a state in which the adhesion layers 61 and 62 before being cured by the chemical change in the thermosetting resin soften by heating, the second adhesion layer 62 is softer than the first adhesion layer 61. When each of the adhesion layers 61 and 62 softens, the temperature of each of the adhesion layers 61 and 62 falls within a predetermined temperature range, any temperature within the predetermined temperature range is 80° C. or more and 400° C. or less.

Next, a manufacturing method of the treatment instrument 1, in particular, a method of attaching the heat generating module 40 including the substrate 41 and the heat generator 42 to the heat transmitting member 32 will be described. In the manufacture of the treatment instrument 1, the substrate front surface 51 becomes uneven by forming the heat generator 42 on the substrate front surface 51 of the substrate 41. The substrate 41 on which the heat generator 42 is formed is disposed on the installation surface 43 of the heat transmitting member 32 in a state in which the substrate front surface 51 faces the heat transmitting member 32 side. As shown in FIG. 4, the first adhesion layer 61 is disposed between the installation surface 43 of the heat transmitting member 32 and the substrate front surface 51 of the substrate 41, and the second adhesion layer 62 is disposed between the substrate front surface 51 of the substrate 41 and the first adhesion layer 61. At this time, the substrate front surface 51 of the substrate 41 is in contact with the second adhesion layer 62, but the substrate 41 is not in contact with the first adhesion layer 61 and the heat transmitting member 32. Also, the second adhesion layer 62 is not inserted into the recess 54, and a gap is formed between the second adhesion layer 62 and the substrate front surface 51 by the recess 54.

The adhesion layers 61 and 62 are heated to raise the temperature of each of the adhesion layers 61 and 62 to the above-mentioned predetermined temperature range. Thereby, each of the adhesion layers 61 and 62 softens by fluidization or the like of the thermosetting resin forming each of the adhesion layers 61 and 62. The second adhesion layer 62 is softer than the first adhesion layer 61 in a state in which each of the adhesion layers 61 and 62 softens by heating. As shown in FIG. 5, with each of the adhesion layers 61 and 62 softened, using a press 65 or the like, the substrate 41 is pressed toward the installation surface 43 of the heat transmitting member 32, and the adhesion layers 61 and 62 are pressurized. At this time, a predetermined pressure is applied to the adhesion layers 61 and 62, and the predetermined pressure is any value of 0.1 MPa or more and 30 MPa or less. As a result, the first adhesion layer 61 is in close contact with the installation surface 43 from the substrate 41 side, and the first adhesion layer 61 is adhered to the installation surface 43 by a fluidized thermosetting resin or the like. In addition, adhesion layers 61 and 62 is in close contact with each other at the boundary B1 of the adhesion layers 61 and 62, and the adhesion layers 61 and 62 are adhered to each other by a fluidized thermosetting resin or the like. The adhesion layers 61 and 62 are slightly mixed to each other by fluidization of the thermosetting resin. However, as mentioned above, in the adhesion layers 61 and 62, at least one of the ingredient of the thermosetting resin, the content of the ceramic, and the size of the ceramic powder is different from each other. For this reason, even if the thermosetting resin is fluidized, the adhesion layers 61 and 62 are maintained in layers, and the adhesion layers 61 and 62 are distinguished from each other by the boundary B1.

In addition, in a state in which each of the adhesion layers 61 and 62 softens by heating, and the substrate 41 is pressed toward the heat transmitting member 32, the second adhesion layer 62 is in close contact with the substrate front surface 51 including the heat generator 42 from the heat transmitting member 32 side, and the second adhesion layer 62 is adhered to the substrate front surface 51 by a fluidized thermosetting resin or the like. At this time, since the second adhesion layer 62 is soft, the second adhesion layer 62 is inserted into the recess 54 of the uneven substrate front surface 51. The second adhesion layer 62 is inserted into the recess 54, so that a gap is less likely to be formed between the second adhesion layer 62 and the uneven substrate front surface 51 to increase the contact area between the second adhesion layer 62 and the substrate front surface 51.

The softened first adhesion layer 61 is harder than the softened second adhesion layer 62, and the first adhesion layer 61 has a certain degree of hardness even in the softened state. For this reason, even if the substrate 41 is pressed toward the heat transmitting member 32 in a state in which each of the adhesion layers 61 and 62 softens, the first adhesion layer 61 is not inserted into the recess 54 of the substrate front surface 51, and the state in which the boundary B1 of the adhesion layers 61 and 62 is positioned closer to the installation surface 43 with respect to the top of any protrusion 53 of the substrate front surface 51 is maintained. Therefore, even in a state in which each of the adhesion layers 61 and 62 softens by heating, and the substrate 41 is pressed toward the heat transmitting member 32, the dimension in the thickness direction is maintained at the thickness T1 of the first adhesion layer 61 or more in any position at the electrically insulating portion 60 between the substrate front surface 51 and the installation surface 43.

Heating of the adhesion layers 61 and 62 is continued in a state in which the first adhesion layer 61 adheres to the installation surface 43, and the second adhesion layer 62 is in close contact with the heat generator 42 and the substrate front surface 51. Thereby, the thermosetting resin which forms each of the adhesion layers 61 and 62 chemically changes to cure each of the adhesion layers 61 and 62. By curing the adhesion layers 61 and 62, the substrate 41 (heat generating module 40) is attached to the installation surface 43 of the heat transmitting member 32 through the adhesion layers 61 and 62. When the adhesion layers 61 and 62 are cured, the heating of the adhesion layers 61 and 62 is stopped. As described above, each of the adhesion layers 61 and 62 does not soften or melt even if it is heated again after cooling, once it is cured by the chemical change in the thermosetting resin.

Next, the function and effects of the treatment instrument 1 of the present embodiment will be described. When performing the treatment using the treatment instrument 1, the operator holds the housing 3 and inserts the end effector 5 into a body cavity such as the abdominal cavity. A treatment target such as a living tissue is disposed between the pair of grasping pieces 11 and 12, and the handle 8 is closed with respect to the grip 7. Thereby, a space between the grasping pieces 11 and 12 is closed, and the treatment target is held between the grasping pieces 11 and 12. With the treatment target between the grasping pieces 11 and 12 held, the operator perform the operation with the operation member 18, and causes the energy source device 17 to output electric energy to the treatment instrument 1. As a result, as aforementioned, a high-frequency current flows between the electrically conductive member 22 and the heat transmitting member 32 through the treatment target, and the heat generated by the heat generator 42 is given to the treatment target from the treating surface 33.

In the present embodiment, since the substrate 41 is attached to the installation surface 43 of the heat transmitting member 32 as described above, the second adhesion layer 62 is inserted into the recess 54 on the uneven substrate front surface 51 as described above. The second adhesion layer 62 is inserted into the recess 54, so that the contact area between the substrate front surface (heat generator 42) and the second adhesion layer 62 is increased. The increase in the contact area between the substrate front surface 51 and the second adhesion layer 62 improves the transfer of heat generated by the heat generator 42 to the second adhesion layer 62. As a result, the heat generated by the heat generator 42 is properly transmitted through the adhesion layers 61 and 62 and the heat transmitting member 32, and the thermal conductivity to the treating surface 33 is secured. The heat generated by the heat generator 42 is appropriately transmitted to the treating surface 33, so that the treatment performance for the treatment using the heat generated by the heat generator 42 is secured.

Also, in the present embodiment, since the substrate 41 is attached to the installation surface 43 of the heat transmitting member 32 as described above, so that the first adhesion layer 61 is not inserted into the recess 54, and the dimension in the thickness direction is equal to or more than the thickness T1 of the first adhesion layer 61 in any position at the electrically insulating portion 60 between the substrate front surface 51 and the installation surface 43. Therefore, by thickening the thickness T1 of the first adhesion layer 61 to some extent, it is possible to suppress the thinning of the electrically insulating portion 60 formed by the adhesion layers 61 and 62. Since the electrically insulating portion 60 does not become thin, the voltage resistance of the electrically insulating portion 60 formed by the adhesion layers 61 and 62 is secured. That is, when a voltage is applied to the electrically insulating portion 60, such as when electric energy is supplied to the heat generator 42 and high-frequency electric power is supplied to the electrically conductive member 22 and the heat transmitting member 32, an electrical breakdown of the electrically insulating portion 60 is effectively suppressed. As a result, electrical conduction between the electrical circuit of the electric energy supplied to the electrically conductive member 22 and the heat transmitting member 32 (high-frequency electric power) and the electrical circuit of electric energy supplied to heat generator 42 (DC power or AC power) is further effectively suppressed.

In an exemplary embodiment shown in FIGS. 6 and 7, the first adhesion layer 61 is in close contact with the substrate side surfaces 55 and 56 of the substrate 41 from the outside in the width direction of the substrate 41. Further, the first adhesion layer 61 is in close contact with the substrate distal surface 57 from the distal side, and is in close contact with the substrate back surface 52 from the back surface 35 side. In the present embodiment, the first adhesion layer 61 is in close contact with the entire substrate back surface 52. Therefore, in this embodiment, in a cross section substantially perpendicular to the direction along the longitudinal axis C, the substrate 41 (heat generating module 40) and the second adhesion layer 62 are covered with the first adhesion layer 61 over the entire circumference.

The first adhesion layer 61 having electrical insulation is in close contact with the substrate side surfaces 55 and 56 of the substrate 41, so that in a state in which electric energy is supplied to the heat generator 42, the discharge through the gap at a boundary B2 between the substrate 41 (substrate front surface 51) and the second adhesion layer 62 is effectively suppressed. As a result, electrical conduction between the heat transmitting member 32 and the heat generator 42 is further effectively suppressed, and the voltage resistance of the electrically insulating portion 60 formed by the adhesion layers 61 and 62 is further improved.

The first adhesion layer 61 may not be in close contact with the entire substrate back surface 52, but may be in contact with only part of the substrate back surface 52. In the present embodiment, for example, the first adhesion layer 61 is not in close contact in a partial region of the substrate back surface 52 in the circumferential direction of the substrate 41. In this embodiment, in the substrate back surface 52, the region which is not in close contact with the first adhesion layer 61 is exposed to cavity 36. Also, although the first adhesion layer 61 may be in close contact with the substrate side surfaces 55 and 56, the first adhesion layer 61 may not be in close contact with the substrate distal surface 57 and the substrate back surface 52. In such embodiments, since the adhesion layer 61 is in close contact with the substrate side surfaces 55 and 56 of the substrate 41, the function and effect same as that of the above discussed embodiments can be obtained.

In the exemplary embodiment shown in FIGS. 8 and 9, instead of the first adhesion layer 61, the second adhesion layer 62 is in close contact with the substrate side surfaces 55 and 56 of the substrate 41 from the outside in the width direction of the substrate 41. The second adhesion layer 62 is in close contact with the substrate distal surface 57 from the distal side and is in close contact with the substrate back surface 52 from the back surface 35 side. In the present embodiment, the second adhesion layer 62 adheres to the entire substrate back surface 52.

In this embodiment, the second adhesion layer 62 having electrical insulation is in close contact with the substrate side surfaces 55 and 56 of the substrate 41. For this reason, as in the above embodiments, in a state in which electric energy is supplied to the heat generator 42, the discharge through the gap at the boundary B2 between the substrate 41 (substrate front surface 51) and the second adhesion layer 62 is effectively suppressed.

The second adhesion layer 62 may not in close contact with the entire substrate back surface 52, but may be in contact with only part of the substrate back surface 52. Also, although the second adhesion layer 62 may be in close contact with the substrate side surfaces 55 and 56, the second adhesion layer 62 may not be in close contact with the substrate distal surface 57 and the substrate back surface 52.

Moreover, in the above-mentioned embodiment and the like, a bipolar treatment is performed in which the heat transmitting member 32 and the electrically conductive member 22 are made to function as electrodes, and a high-frequency current is caused to flow through the treatment target between the heat transmitting member 32 and the electrically conductive member 22. However, it is not limited to this. For example, the grasping piece 11 may not be provided, and a treating section having a configuration same as that of the grasping piece 12 may be provided at the distal portion of the shaft 2. In this case, a system in which the treatment instrument 1 is used includes a return electrode (not shown), and in the treatment, the return electrode is attached to the human body outside the body. In the present embodiment, high-frequency electric power is supplied from the energy source device 17 to the heat transmitting member 32 and the return electrode plate. A monopolar treatment is performed in which a high-frequency current is caused to flow through the treatment target between the treating surface 33 of the heat transmitting member 32 and the return electrode plate. Also in the present embodiment, when the electric energy (DC power or AC power) is supplied to the heat generator 42, heat is generated in the heat generator 42. The heat generated by the heat generator 42 is transmitted to the treating surface 33 through the second adhesion layer 62, the first adhesion layer 61, and the heat transmitting member 32 in this order, and is given to the treatment target from the treating surface 33.

In the above embodiment and the like, the heat transmitting member (32) of the treatment instrument (1) includes the treating surface (33) and the installation surface (43) opposite to the treating surface (33), and has electrical conductivity and thermal conductivity. Due to the supply of electric energy, the heat transmitting member (32) functions as an electrode. In addition, the heat generator (42) is formed on the substrate front surface (51) of the substrate (41), and the heat generator (42) generates heat when electric energy is supplied. The substrate (41) is attached to the installation surface (43) of the heat transmitting member (32) in a state in which the substrate front surface (51) faces the heat transmitting member (32) side, and the substrate front surface (51) of the substrate (41) is formed unevenly by the heat generator (42). The first adhesion layer (61) is provided between the installation surface (43) of the heat transmitting member (32) and the substrate (41), and the second adhesion layer (62) is provided between the substrate (41) and the first adhesion layer (61). Each of the adhesion layers (61, 62) is formed of a material having thermal conductivity and electrical insulation. The first adhesion layer (61) is in close contact with the installation surface (43) of the heat transmitting member (32), and the second adhesion layer (62) is in close contact with the heat generator (42) and the substrate front surface (51) in a state in which it is inserted in the recess (54) formed on the uneven substrate front surface (51).

Additional advantages and modifications will readily occur to those skilled in the art. Therefore, the present disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment instrument comprising:
   a heat transmitter having thermal conductivity and including a treating surface and an installation surface opposite to the treating surface;
   a heat generator configured to generate heat when electric energy is supplied;
   a substrate including a substrate front surface on which the heat generator is formed, the substrate being attached to the installation surface of the heat transmitter such that the substrate front surface faces the heat transmitter, the substrate front surface and the heat generator together forming an uneven surface including a recess;
   a first adhesion layer provided between the installation surface of the heat transmitter and the substrate, the first adhesion layer being formed of a material having thermal conductivity and electrical insulation, the first adhesion layer being in contact with the installation surface of the heat transmitter; and
   a second adhesion layer provided between the substrate and the first adhesion layer, the second adhesion layer being formed of a material having thermal conductivity and electrical insulation, the second adhesion layer being in contact with the heat generator and the substrate front surface such that the second adhesion layer is inserted into the recess of the uneven surface formed by the heat generator on the substrate front surface,
   wherein:
   each of the first adhesion layer and the second adhesion layer is formed of a material that softens by heating and is cured by continuing the heating after the softening, and
   the second adhesion layer is configured to be softer than the first adhesion layer when the first adhesion layer and the second adhesion layer are softened by the heating.

2. The treatment instrument according to claim 1, wherein:
   the first adhesion layer and the second adhesion layer are each formed of a mixture of a thermosetting resin and a ceramic powder, and
   at least one of: an ingredient of the thermosetting resin, a content of the ceramic powder, and a size of the ceramic powder is different in the first adhesion layer and the second adhesion layer.

3. The treatment instrument according to claim 1, wherein the first adhesion layer is not inserted into the recess of the uneven surface.

4. The treatment instrument according to claim 1, wherein the uneven surface formed by the substrate front surface and the heat generator does not contact the first adhesion layer or the heat transmitter.

5. The treatment instrument according to claim 1, wherein a boundary between the first adhesion layer and the second adhesion layer is positioned on an installation surface side of any protrusion of the uneven surface formed by the substrate front surface and the heat generator.

6. The treatment instrument according to claim 1, wherein:
   the first adhesion layer and the second adhesion layer together form an electrically insulating portion between the uneven surface and the installation surface,
   the electrically insulating portion has a dimension in a thickness direction equal to or greater than a thickness T1 of the first adhesion layer at any position, and
   the thickness direction is a stacking direction of the first adhesion layer, the second adhesion layer, and the substrate.

7. The treatment instrument according to claim 1, further comprising a grasping piece facing the treating surface of the heat transmitter, the grasping piece being openable and closable with respect to the heat transmitter,
   wherein:
   the heat transmitter has electrical conductivity, and is configured to function as an electrode when electric energy is supplied, and
   the grasping piece includes an electrically conductive member that is configured to function as an electrode different from the heat transmitter when electric energy is supplied.

8. The treatment instrument according to claim 1, wherein the substrate includes a first substrate side surface disposed at one side in a width direction of the substrate, and a second substrate side surface disposed opposite to the first substrate side surface.

9. The treatment instrument according to claim 8, wherein the first adhesion layer is also disposed on an outer side of the substrate in the width direction so as to contact the first substrate side surface and the second substrate side surface.

10. The treatment instrument according to claim 9, wherein the width direction of the substrate is orthogonal to:
    a stacking direction of the first adhesion layer, the second adhesion layer, and the substrate, and
    a longitudinal axis of the heat transmitter.

11. The treatment instrument according to claim 10, wherein the first adhesion layer further contacts a substrate back surface opposite to the substrate front surface.

12. The treatment instrument according to claim 8, wherein the second adhesion layer is also disposed on an outer side of the substrate in the width direction so as to contact the first substrate side surface and the second substrate side surface.

13. The treatment instrument according to claim 12, wherein the width direction of the substrate is orthogonal to:
- a stacking direction of the first adhesion layer, the second adhesion layer, and the substrate, and
- a longitudinal axis of the heat transmitter.

14. The treatment instrument according to claim 13, wherein the first adhesion layer further contacts a substrate back surface opposite to the substrate front surface.

15. A method of manufacturing a treatment instrument, the method comprising:
- forming a heat generator on a substrate front surface of a substrate such that the substrate front surface and the heat generator together form an uneven surface including a recess;
- disposing the substrate on an installation surface of a heat transmitter having electrical conductivity and thermal conductivity such that:
  - the substrate front surface faces the installation surface of the heat transmitter, the installation surface being opposite to a treating surface of the heat transmitter,
  - a first adhesion layer formed of a material having thermal conductivity and electrical insulation is disposed between the installation surface of the heat transmitter and the substrate, and
  - a second adhesion layer formed of a material having thermal conductivity and electrical insulation is disposed between the substrate and the first adhesion layer;
- heating the first adhesion layer and the second adhesion layer to soften the first adhesion layer and the second adhesion layer, and thereby forming a state in which the second adhesion layer is softer than the first adhesion layer;
- pressing the substrate toward the heat transmitter in a state in which the first adhesion layer and the second adhesion layer have been softened to insert the second adhesion layer into the recess formed in the uneven surface; and
- continuing heating of the first adhesion layer and the second adhesion layer in a state in which the first adhesion layer is in contact with the installation surface and the second adhesion layer is in contact with the heat generator and the substrate front surface to cure the first adhesion layer and the second adhesion layer, and thereby attaching the substrate to the installation surface of the heat transmitter through the first adhesion layer and the second adhesion layer.

16. The method according to claim 15, wherein the first adhesion layer is not inserted into the recess of the uneven surface when the substrate is pressed toward the heat transmitter.

17. The method according to claim 15, wherein:
- the first adhesion layer and the second adhesion layer together form an electrically insulating portion between the uneven surface and the installation surface,
- when the substrate is pressed toward the heat transmitter, a dimension in a thickness direction is maintained at a thickness equal to or greater than a thickness $T1$ of the first adhesion layer at any position of the electrically insulating portion between the uneven surface and the installation surface, and
- the thickness direction is a stacking direction of the first adhesion layer, the second adhesion layer, and the substrate.

18. The method according to claim 15, wherein the substrate is pressed toward the installation surface by a predetermined pressure in a range of from 0.1 MPa to 30 MPa.

* * * * *